(12) United States Patent
Lefevre et al.

(10) Patent No.: US 6,184,213 B1
(45) Date of Patent: Feb. 6, 2001

(54) DILUENT AND DISINTEGRATING COMPOSITION, ITS METHOD OF ACHIEVEMENT AND ITS USE

(75) Inventors: Philippe Lefevre, Merville; Claude Quettier, La Gorgue, both of (FR)

(73) Assignee: Roquette Freres, Lestrem (FR)

( * ) Notice: Under 35 U.S.C. 154(b), the term of this patent shall be extended for 0 days.

(21) Appl. No.: 09/328,064

(22) Filed: Jun. 8, 1999

(30) Foreign Application Priority Data

Jun. 8, 1998 (FR) .................................................. 98 07175

(51) Int. Cl.$^7$ ...................................................... A61K 31/70
(52) U.S. Cl. .............................. 514/60; 536/102; 536/124
(58) Field of Search ..................... 514/60, 54; 536/102, 536/124

(56) References Cited

U.S. PATENT DOCUMENTS 4,369,308  1/1983  Trubiano et al. .
5,131,953 * 7/1992  Kasica et al. .......................... 127/65
5,164,014  11/1992 Brancq et al. .

FOREIGN PATENT DOCUMENTS 1216873  12/1970  (GB) .

OTHER PUBLICATIONS

Abstract of FR 2 661 317 (WPIL), Oct. 31, 1991.
Visavarungroj. et al., 1992, Pharm. Tech. Int., Jan./Feb p. 26–32.
Database WPI XP002093553 & JP 57 131274 A, 1982.

* cited by examiner

Primary Examiner—Elli Peselev
(74) Attorney, Agent, or Firm—Henderson & Sturm LLP

(57) ABSTRACT

The present invention relates to a diluent and disintegrating composition containing an effective proportion of intact grains of amylose rich starch enclosed in a pre-gelatinised starch matrix. The present invention also relates to a process for producing this composition as well as its use in the manufacture of solid shapes.

12 Claims, 2 Drawing Sheets

COMPOSITION 1B

Scanning Electron Microscopy

Magnification: X55

Magnification: X345

Magnification: X730

Magnification: X730

COMPOSITION 1A

Scanning Electron Microscopy

Magnification: X55.

Magnification: X365.

Magnification: X730.

DILUENT AND DISINTEGRATING COMPOSITION, ITS METHOD OF ACHIEVEMENT AND ITS USE

CROSS-REFERENCE TO RELATED APPLICATIONS

Not Applicable.

STATEMENT REGARDING FEDERALLY SPONSORED RESEARCH OR DEVELOPMENT

Not Applicable

BACKGROUND OF THE INVENTION

1. Field of the Invention

The object of the invention is a diluent and disintegrating composition. It also covers a method for obtaining this composition as well as its industrial use, for the manufacture of solid shapes.

2. Description of the Prior Art

By the expression "solid shapes" is meant every presentation of powder(s) in the form of tablets, pellets, capsules, microspheres or granules. The solid shapes consist mainly of inert materials, grouped together under the term of excipients, as a complement to one or more active pharmaceutical, cosmetic, foodstuff, chemical or agrochemical substances, such as flavourings, perfumes, detergents, pesticides, antibiotics, enzymes, vitamins. These excipients are generally classified according to their principal function(s), that is how diluents, or filling agents, binders which ensure cohesion of the ingredients, disintegrators which enable the destruction of the physical integrity of the solid shapes when these are placed in an appropriate fluid are distinguished. Other excipients can be added in parallel, particularly lubricants in order to improve the flowing properties of the powders. A good powder diluent must possess the following properties:

chemical compatibility with the active substance, free flow, to enable an even filling of the matrices in the modern high rate shaping machines, granulometry adapted to that of the active substance, in order to ensure a constant dosage, absence of dust, to facilitate handling, to avoid clogging and to limit the risks of explosion, high density, to promote the flow and limit the size of the final solid shape, cohesion, to ensure the physical stability of the solid shapes.

A good disintegrator must ensure a rapid availability of the active substances, whilst having satisfactory rheological properties.

The formulator wishes to have a principal excipient possessing optimum properties, which he will make up as a function of the characteristics of the solid shape which he wishes to develop, with one or more secondary excipients. There does not exist any universal excipient having all the previously described properties.

Starch and its derivatives form part of the chosen excipients, giving a wide spectrum of performance for the formulation of solid shapes.

In the natural state, starch comes in the form of granules, the diameter of which varies approximately between 1 and 100 μm.

Its availability and its low cost, as well as its natural origin are the principal factors favouring its use. The majority of the commercial starches come from maize, but wheat and potato are also significant sources. Other sources are known, like rice, manioc, peas. Starch consists of two types of α-D-glucose polymers, amylose and amylopectin, which have a different structure : amylose is a linear polymer, whilst amylopectin possesses a ramified structure.

Most of the starches, coming from maize, from wheat or from potato, contain 18 to 28% of amylose.

In the manufacture of solid shapes, starch is used as diluent, binder or disintegrator.

Natural starch offers, on its own, a limited number of applications. Indeed, when it is used as a direct compression diluent, its compressibility is insufficient to enable the manufacture of tablets of satisfactory hardness.

Actually, in the particular case of compression, the particles undergo a deformation, which can be of different types according to their nature : elastic or plastic deformation.

during an elastic deformation, the deformation disappears when the force ceases to be applied.

This deformation is not favourable to producing tablets, since the particles regain their initial state at the end of compression. This is particularly the case for natural starches.

during a plastic deformation, on the other hand, the deformation persists when the force ceases to be applied, this being entirely favourable to the production of tablets.

Moreover, natural starch possesses poor flow properties, which makes it inadvisable in formulations for direct compression. This is due to the small size of its particles as well as its low density. The fluidity of the formulations is an essential criterion on which depends the weight uniformity of the completed tablets. On the other hand, natural starch possesses good disintegrating properties. Indeed, starch granules swell in the presence of water, which causes the rupture of the structure in which they are contained, and therefore its disintegration.

Natural starch can be modified in a simple and inexpensive manner by a thermal process causing the rupture of the granules and a partial hydrolysis of the polymeric chains. A pre-gelatinised starch is then produced which, in powder form and for a selected granulometry, is a good flowing and compressing product, but possessing a practically zero disintegrating power. It is preferably used as a binder for powders.

Chemical modifications, such as reticulation, described in the U.S. Pat. No. 4,369,308, can be made to pre-gelatinised starch, but these lead to a poor quality disintegrating agent.

Taking account of the fact that the properties of pre-gelatinised starch and of natural starch are diametrically opposite but nevertheless jointly required in numerous solid shapes, a simple mixture of the two powders would have to be considered. However, these two starches possess granulometries which are very different from each other, which causes a rapid "unmixing" of the powders from the slightest handling, and a very varying homogeneity of the final solid shape, which is industrially unacceptable.

In the patent FR 1, 583 232, a compacting process leading to a partially pre-gelatinised starch has therefore been proposed. The product produced according to this procedure, and marketed under the name STARCH 1500®, possesses good binding and diluent properties, but its disintegrating power remains limited, and its flow properties are mediocre, which requires the use by the formulators of complementary excipients (VISAVARUNGROJ N, RENON J. P., (1992) Pharm. Tech. Int. JAN/FEB p26–32).

Moreover, the implementation of this complex and expensive process does not enable a good control of the granulometry, which causes a large variation in the properties of this product.

More recently, another process for producing directly compressible pre-gelatinised starch has been proposed, in the patent EP 402 186. The product produced, marketed under the name of SEPISTAB® ST 200, results from a moist granulation of natural starch by a starch solution. This process, which requires a large proportion of natural starch, leads to a powder, the granules of which are flaky and fragile, which is detrimental to the use of this powder in high rate industrial machines, which generate a significant physical stress.

Consequently, none of the prior art processes enable, in an acceptable economic way, starch compositions simultaneously having good diluent and disintegrating properties to be produced.

BRIEF SUMMARY OF THE INVENTION

The object of the invention is therefore to remedy the disadvantages of the prior art and to supply a diluent and disintegrating starch composition meeting the various practical requirements better than those which exist already.

DETAILED DESCRIPTION OF THE INVENTION

Figure 1:
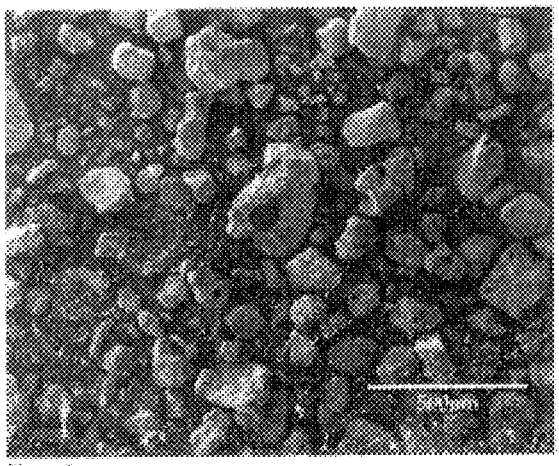
FIGS. 1–7 represent observations by an electron microscope of the compositions 1A and 1B according to Example 1

Applicants have been successful in finding that this object was attained as soon as a pre-gelatinised starch containing a significant content of intact amylose rich starch granules is used.

To be more precise, the diluent and disintegrating composition according to the invention is characterised by the fact that it contains an effective proportion of intact amylose rich starch granules enclosed in a pre-gelatinised starch matrix.

The invention relates also to a preparation process of a diluent and disintegrating composition possessing the characteristics stated below.

The effective proportion is designated as that necessary and sufficient to obtain the requisite effect, i.e. good diluent and disintegrating properties.

By the term "pre-gelatinised starch", is meant every starch having undergone a thermal process in the presence of water, so that it loses its granular structure, and becomes more or less soluble in cold water. By "starch" is meant the starches of all origins, natural or hybrid, modified or not, and any of their mixtures.

By the term "amylose rich starch" is designated every starch having an amylose content at least equal to 50%, as in particular the maize starches marketed by the Applicant Company under the trade name EUROLYN®.

The diluent and disintegrating composition according to the invention is constituted by intact amylose rich starch granules, i.e. non ruptured, which are totally or partially coated with pre-gelatinised starch, this latter having lost its granular structure. The particular nature of this composition gives it alone all the properties required in the formulation of solid shapes, properties which has never until then been combined in the same product with the prior art. This enables numerous applications of the composition according to the invention to be seen in a new light, in particular in the manufacture of tablets, capsules, granules or any other solid shape likely to require an excipient possessing the aforesaid properties. On the other hand, amylose rich starch has a thermal and mechanical resistance greater than standard starches, which enables sterilisation, granulation-drying treatments to be considered, or any other treatments carried out on the solid shape in the form of a physical stress.

According to a preferential characteristic, the diluent and disintegrating composition according to the invention contains a proportion of amylose rich starch of between 20 and 90%, this percentage being calculated by weight relative to the total weight of amylose rich starch and of pre-gelatinised starch contained in the aforesaid composition. Preferably, this proportion is between 30 and 80%.

The Applicant has indeed revealed, after long research, that this second characteristic enabled the advantageous obtaining of good diluent and disintegrating properties to be produced at the same time.

Thus, with over 90% amylose rich starch in the composition, it becomes generally impossible to form a pre-gelatinised starch matrix enclosing amylose granules, and in the same way, to obtain all the properties characterising the composition according to the invention. On the other hand, below 20% of amylose rich starch, the disintegrating properties are not generally satisfactory.

With regard to the apparent density of the composition according to the invention, which represents a significant criterion for the formulator, this is advantageously greater than 0.5 g/ml.

The apparent density before compression has been measured according to the analytical method 2.9.15 of the Pharmacopée Européenne, 3rd edition.

The principle of this measurement rests on the determination of the volumes before and after compression of the powders and makes use of an apparatus consisting of a compressing device provided with a graduated burette, the said apparatus causing successive drops from the burette containing the powder to be tested.

The Applicant has thus revealed that an apparent density at least equal to 0.5 g/ml enabled a particularly satisfactory flow of the composition according to the invention to be produced, and that for its use particularly in the filling of capsules, a high density enabled the size of the capsule to be reduced, which is strongly indicated for facilitating its ingestion by the patient in the case of pharmaceutical capsules. A diluent and disintegrating composition containing at least 10% by weight of totally pre-gelatinised starch, this percentage being expressed relative to the total weight of starch contained in the aforesaid composition, and having an apparent density greater than 0.5 g/ml, constitutes a new product, which is distinguished from pre-gelatinised starches of the prior art.

The Applicant has moreover revealed that the granulometry of the composition according to the invention was able to take place over a very wide range, without the diluent and disintegrating properties being affected. This characteristic has been calculated from the failures produced by sieving on successive sieves with decreasing apertures. The mean granulometry of the composition according to the invention can in particular be between 50 $\mu$m and 1000 $\mu$m.

This enables the granulometry of the composition according to the invention to be adapted, at will and advantageously, to that of the active substance, whilst retaining all of the previously quoted properties.

The diluent and disintegrating compositions according to the invention are likely to be produced in many variants but all particularly according to a process comprising the following stages:

preparation of a starch milk and of amylose rich starch,
cooking this milk at a temperature lower than 130° C. and preferably less than 110° C. so as to obtain a paste,
drying this paste,
grinding this dried paste,
recovery of the diluent and disintegrating composition thus produced.

The characteristics can be adjusted by modifying the proportion of amylose rich starch in the initial milk.

With regard to the preparation of the milk, it is preferred that this should have a dry material of at least 30%.

The cooking and drying stages can be implemented by any technique known to the person skilled in the art.

With regard to the cooking temperature of the milk, it is preferred that it should be close to 100° C.

In the same way, the grinding is conducted according to any type of known technique enabling a powder possessing the requisite granulometric characteristics to be produced.

According to an advantageous version of the process according to the invention, a milk is prepared containing from 20 to 90%, and preferably from 30 to 80%, of amylose rich starch, this percentage being expressed by weight of amylose rich starch relative to the total weight of starches contained in the milk.

According to an advantageous embodiment of the above mentioned process, the cooking temperature of the starch milk is between 80 and 105° C.

The Applicant Company has demonstrated that it is able to advantageously manufacture the composition according to the invention by using a drum dryer. Such equipment enables on one and same device the cooking and drying stages of the process according to the invention to be reproduced.

This well known equipment permits, in effect, by using the heat transferred from the surface of the steam heated drums to the starch milk, the gelatinisation of this milk, which is spread uniformly in a thin film on the hot surface of the drum by applicators.

The film thus formed is then scraped with the help of a scraper knife, so as to lift off a sheet which is then ground to obtain a composition in conformity with the invention.

An important advantage of the process according to the invention lies in the fact that its implementation applied to the starch milk according to the invention is simple and inexpensive. It enables moreover a homogeneous composition to be produced, consisting of intact amylose rich starch grains enclosed in a pre-gelatinised starch matrix, which does not risk causing segregation during the process for the manufacture of solid shapes. Moreover, the process enables a wide range of disintegrating compositions according to the invention to be produced, by adjusting the proportions, within the mixture, of the starch and amylose rich starch, without this being detrimental to the diluent properties of the aforesaid compositions. Furthermore, it is possible, at any time in this process, including before, during and/or after the grinding stage described above, to put the amylaceous composition in the presence of one or several non-amylaceous constituents such as, for example, active substances, conservatives, excipients, having or not having diluent or disintegrating properties, since such constituents do not damage the requisite properties of the final mixture.

In any case, the compositions according to the invention possess diluent and disintegrating properties greater than those of the amylaceous products of the prior art.

A possible explanation of these noteworthy properties is that the cooking-drying process applied to the starch milk, causes an unexpected compacting of the mixture, always retaining the intact amylose rich starch granules in effective proportion which ensures, for them, the requisite disintegrating power, and an increased physical resistance.

The composition according to the invention can thus be used to advantage in the manufacture of solid shapes, as a diluent and disintegrating agent, whether in the food, pharmaceutical, cosmetic, chemical or agro-chemical fields.

The advantages of this invention will be better understood by reading the following examples and the figures which relate to them, given as purely illustrative examples.

EXAMPLE 1

Preparation of compositions according to the invention and comparison with compositions of the prior art Two compositions are prepared containing respectively 50 and 75% amylose rich starch in the following conditions:

Composition 1A:
  50% standard maize starch
  50% of Eurylon®
Composition 1B:
  25% of standard maize starch
  75% of Eurylon®
Dry matter of the milks:
  35%

Each milk thus prepared is cooked on the single cylinder drum dryer, at a temperature of 100° C.

The principal physical characteristics of the compositions 1A and 1B thus produced are given in the following table, in comparison with a standard maize starch and a pre-gelatinised maize starch marketed by the Applicant under the trade name LYCATAB PGS®.

|  | A1 | 1B | Maize starch | LYCATAB PGS |
|---|---|---|---|---|
| Mean diameter (1) (microns) | 85 | 90 | 13.8–14.5 | 90 |
| Apparent density before compacting (2) g/ml | 0.65 | 0.64 | 0.43 | 0.45 |
| Aptitude to flow (3) (seconds) | 5 | 6 | ind. | 9 |
| Amylose rich starch content (% dry matter) | 50 | 75 | 0 | 0 |
| Standard starch content (% dry matter) | 50 | 25 | 100 | 100 |

(1) The mean diameter is calculated from the granulometry measured by sieving on successive sieves of 200, 100, 80, 63 and 40 microns, except for the maize starch, the sampled value of which is that quoted in WHISTLER R. L., BEMILLER J. N., PASCHALL E. F., (1984), Starch Chem. and Techn., $2^{nd}$ ed.

(2) The apparent density is measured according to the pharmaceutical technology method 2.9.15 of the Pharmacopëe Europëenne, $3^{rd}$ edition.

(3) The flow aptitude is measured according to the pharmaceutical technology method 2.9.16 of the Pharmacopëe Europëenne, $3^{rd}$ edition.

It is concluded from these results, that the compositions according to the invention possess an apparent density greater than the products of the prior art, and a better flow aptitude.

Figure 2:
Figure 3:
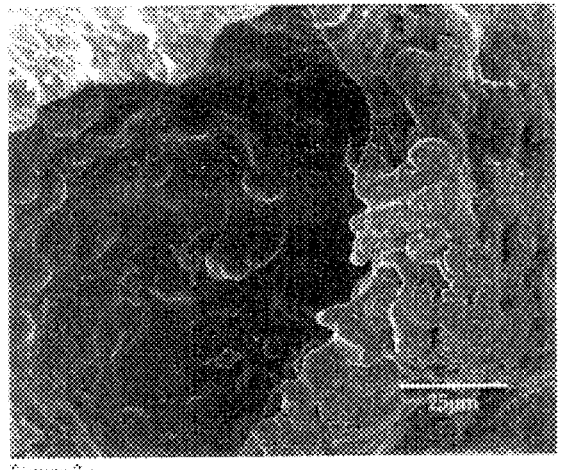
Figure 4:
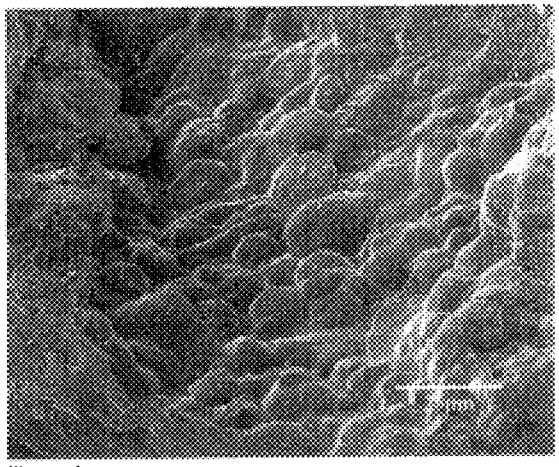
Figure 5:
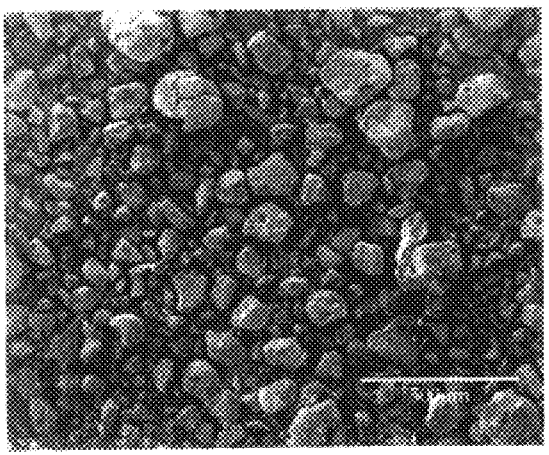
Figure 6:
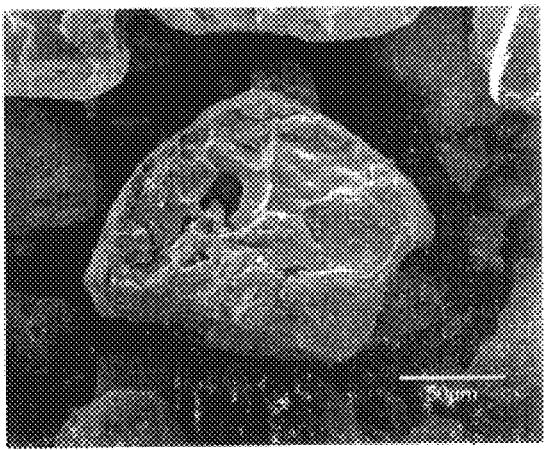
Figure 7:
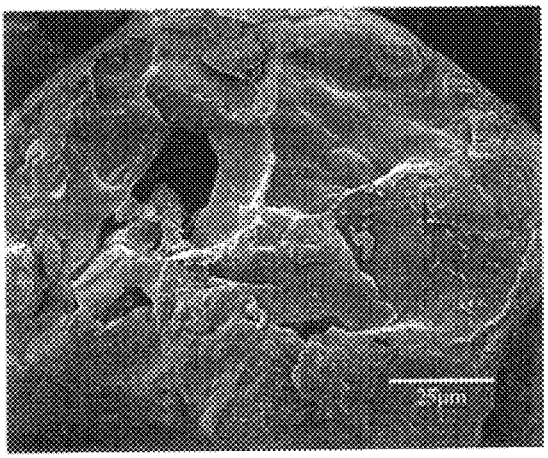

FIGS. 1 to 7

Observation by electron microscope of the compositions 1A and 1B according to Example 1.

The observed compositions show a very different appearance from the ordinary pre-gelatinised starches : they have rounded granular type shapes. The amylose rich starch granules are particularly visible in composition 1B, they are clearly visible in the cavities. These granules are covered with de-structured starch.

EXAMPLE 2

Evaluation of the disintegrating power of compositions prepared according to Example 1. Comparison with compositions of the prior art.

The disintegrating properties are evaluated according to the following test:

On an alternating press of type FROGERAIS AM, flat tablets are made, of diameter 13 mm, thickness 5 mm, weight 1 g and the following composition:

composition 1A or 1B according to Example 1.
dehydrated dicalcic phosphate for direct compression (EMCOMPRESS®): 50%
magnesium stearate: 0.5%
(ENCOMPRESS® is marketed by the MENDELL Company).

The disintegration times of these tablets are measured according to the pharmaceutical technology method 2.9.1. of the Pharmacopëe Europëenne, $3^{rd}$ edition.

The disintegration times indicated below are the times necessary for the total disintegration of the tablet.

| Products | 1A | 1B | Pre-gelatinised starch | STARCH 1500 |
|---|---|---|---|---|
| Disintegration times | 2 min 50 s | 1 min 45 s | >15 min | 2 min 45 s |

It is concluded from these results that the compositions according to the invention possess a marked disintegrating function, equivalent to the compositions of the prior art where the EURYLON® content is 50%, greater for a content of 75% of EURYLON®.

The amylose granules enclosed in the pre-gelatinised starch matrix have therefore a disintegrating function sufficient to oppose the binding action of the pre-gelatinised starch.

EXAMPLE 3

Evaluation of the compositions according to the invention in the filling of capsules. Comparison with compositions of the prior art.

A core is made for filling the capsules in the following way: a metal matrix, through which a cylindrical vertical hole of diameter 6.3 mm and height of 50 mm is passed, is used.

At first, the lower end of the hole is closed by a metal plate. Then 0.78 ml of the starch compositions described in Example 1 or of products of the prior art is poured, to all of which is previously added 0.5% of magnesium stearate.

Secondly, a force is exerted by means of a punch on the powder until a core sufficiently cohesive to be handled is produced.

Thirdly, the metal plate which blocks the lower end of the hole is removed and the core is ejected into a capsule which is then closed.

The measurements carried out are the initial weight of the powder corresponding to 0.78 ml of filling, the final density of the core, and the disintegration time of the capsule containing the core. This disintegration time is measured according to the pharmaceutical technology method 2-9-2 of the Pharmacopëe Europëenne, $3^{rd}$ edition. The time indicated is that necessary for the total dissolution of the capsule envelope and of total disintegration of the core.

| | 1A | 1B | Pre-gelatinised maize starch LYCATAB PGS | STARCH 1500 |
|---|---|---|---|---|
| Initial weight of powder (in g) | 0.54 | 0.53 | 0.37 | 0.48 |
| Final density of core | 1.02 | 0.99 | 0.86 | 0.89 |
| Disintegration time of the complete capsule | 5 min 30 s | 3 min 20 s | >60 min | 10 min |

The values of the initial weight of powder and final density of the core for the compositions according to the invention are greater than those of compositions of the prior art.

These characteristics are particularly attractive since they enable for the same weight of contents and therefore of the same active dosage the size of the capsules, which are produced by planing (in relation to the initial powder weight) or on machines equipped with a measuring disc or compression measure (in relation to the final density of the core) to be decreased.

A small capsule size is beneficial to the treatment because it helps the patient to adhere to it.

It is particularly noteworthy that this increase in density is not achieved to the detriment of the disintegration : compositions according to the invention give disintegrations slightly more rapid than the compositions of the prior art.

EXAMPLE 4

Evaluation of the compressibility of a composition according to the invention.

Tablets are prepared from a composition according to the invention, containing 50% of EURYLON® to which is added 0.5%, by weight, magnesium stearate as a lubricant.

The compression is carried out by means of an alternating FROGERAIS press of type AM. This press is equipped with round punches with concave faces, with a diameter equal to 13 mm.

The recess of the upper punch and the filling volume of the matrix is adjusted on the press, so as to obtain tablets of 5 mm thickness and density of 1.14.

The hardness of the tablets is measured by using a SCHLEUNIGER-2E hardness meter.

The composition according to the invention, containing 50% EURYLON® has an entirely satisfactory compressibility. This is shown by a hardness of 105N.

It is particularly noteworthy that such a hardness was produced with magnesium stearate which is considered unsuitable for the lubrication and the compression of amylaceous derivatives.

EXAMPLE 5

Evaluation of the wet granulation binding power of composition according to the invention The composition according to Example 1A is used as a moist granulation binder in the following formula:

| Fine crystallised Paracetamol (RHODAPAP/RHONE POULENC) | 250.0 g |
|---|---|
| Standard maize starch (ROQUETTE) | 19.5 g |

-continued

| | |
|---|---|
| Composition of example 1A | 36.8 g |
| Water | 70.0 g |

The granules are prepared in the following way: the three powders are mixed in a planetary mixer at minimum speed for 5 minutes, the water is slowly sprayed on the moving powders. Then the whole is transferred into a high shearing mixer and mixed at very high speed for 5 minutes.

Finally, the granules produced are dried for 30 minutes at 30° C. in a fluidised air bed drier (AEROMATIC).

The initial powder mixture has less than 15% of particles of a size greater than 200 microns.

The granules produced have the following granulometry:
greater than 200 μm: 95.5%
greater than 315 μm: 84.1%
greater than 500 μm: 35.0%

The comparison of the initial granulometry of the mixture of powders and of the granulometry of the granules shows that the compositions according to the invention have a real moist granulation binding power.

They can therefore be used to advantage for the production of granules which can later be transformed into tablets after grading, lubricating and compression on a compression press.

EXAMPLE 6

Evaluation of the friability of the compositions according to the invention. Comparison with the compositions of the prior art.

Friability is measured by using the following test:
15 g of powder are placed in the drum of a ERWEKA TA friability meter (equipped with a drum (with 12 fins) of 19.5 cm diameter). Five steel balls of 16.7 mm diameter and total weight of 94.3 g are added. The whole is rotated for 30 minutes.

The percentages of particles less than 100 microns are measured before and after this test.

The increase in this percentage after this test gives the friability of the powder.

| Particles less than 100 μm | 1A | SEPISTAB ST 200 |
|---|---|---|
| Percentage before test | 58.8 | 31.2 |
| Percentage after test | 58.9 | 40.3 |
| Increase (friability) | 0% | 29.20% |

Contrary to the product of the prior art, the compositions according to the invention are not flaky, which is an undeniable advantage. The user would be able to subject the powder to one or more mechanical stressing processes, if necessary over a very long time without the risk of the appearance of dusts which are to be avoided as much during the compression processes as in the capsule filling. Furthermore, the absence of friability is evidence of the preservation of the basic properties of the powder : granulometry, flow, density before and after compacting, and whatever treatments are undergone.

The compositions according to the invention therefore combine to advantage the properties which had never, until now, been found simultaneously within the same amylaceous composition. They in fact possess diluent and disintegrating properties at the same time, i.e., in other terms, high density, good flow properties, suitable granulometry, rapid disintegration, and a practically zero friability.

What is claimed is:

1. A diluent and disintegrating composition containing an effective proportion of intact amylose rich starch granules enclosed in a pregelatinized starch matrix.

2. The composition according to claim 1 comprising between about 20% to about 90% by weight of amylose rich starch, the percentage being expressed relative to the total starch weight contained in the aforesaid composition.

3. The composition according to claim 2 comprising between about 30% to about 80% by weight of amylose rich starch, the percentages being expressed relative to the total starch weight contained in the aforesaid composition.

4. The composition according to claim 1, having at least one of an apparent density greater than 0.5 g/ml, and a mean granulometry between about 50 μm and about 100 μm.

5. A process for obtaining a composition according to claim 1 comprising:

preparing a milk of starch and amylose rich starch, cooking the milk thus produced at a temperature less than 130° C. so as to obtain a paste, drying aforesaid paste, grinding the dried paste, collecting the diluent and disintegrating composition thus produced, wherein the cooking and drying of the starch milk is carried out on a drum drier.

6. The process according to claim 5, wherein the milk contains between about 20% to about 90% by weight of amylose rich starch, the percentages being expressed relative to the total weight of the starch and amylose rich starch contained in the milk.

7. The process according to claim 6, wherein the milk contains between about 30% to about 80% by weight of amylose rich starch, the percentages being expressed relative to the total weight of the starch and amylose rich starch contained in the milk.

8. The process according to claim 5, wherein the cooking temperature of the milk is between about 80° C. and about 105° C.

9. The process according to claim 5, wherein the dried paste is ground so as obtained a granulometry between about 50 μm and about 1000 μm.

10. A solid shape comprising a composition according to claim 1.

11. A solid shape comprising a composition produced by the process according to claim 5.

12. The process according to claim 5, wherein the cooking temperature of the milk is less than 110° C.

* * * * *